United States Patent [19]

Behrmann et al.

[11] 4,041,100
[45] Aug. 9, 1977

[54] CATALYTIC ALKYLATION UTILIZING OLEFINIC, CONJUGATED CYCLIC HYDROCARBONS AS PROMOTER THEREIN

[75] Inventors: William C. Behrmann; Earl E. Turner, both of Baton Rouge, La.; Victor C. Bastron, Seabrook, Tex.

[73] Assignee: Exxon Research and Engineering Company, Linden, N.J.

[21] Appl. No.: 642,539

[22] Filed: Dec. 19, 1975

[51] Int. Cl.$^2$ ............................................... C07C 3/54
[52] U.S. Cl. .......................... 260/683.47; 260/683.58
[58] Field of Search ...................... 260/683.47, 683.58, 260/683.43, 683.59

[56] References Cited

U.S. PATENT DOCUMENTS

| | | | |
|---|---|---|---|
| 2,313,103 | 3/1943 | Thomas | 260/683.58 |
| 3,766,293 | 10/1973 | Parker et al. | 260/683.58 |
| 3,887,635 | 6/1975 | Parker et al. | 260/683.58 |
| 3,925,318 | 12/1975 | Parker et al. | 260/683.58 |

*Primary Examiner*—George J. Crasanakis
*Attorney, Agent, or Firm*—John W. Ditsler

[57] ABSTRACT

High octane alkylate can be obtained by alkylating a paraffin with an olefin in the presence of an organic promoter and an alkylation catalyst comprising (1) a strong acid such as halosulfuric acid, trihalomethanesulfonic acid or mixtures thereof and (2) a moderator having at least one oxygen atom per molecule. The amount of organic promoter required to produce an alkylate of enhanced octane has been found to vary with reaction temperature at temperatures above about 0° F. A preferred alkylation catalyst comprises fluorosulfuric acid and water.

16 Claims, 1 Drawing Figure

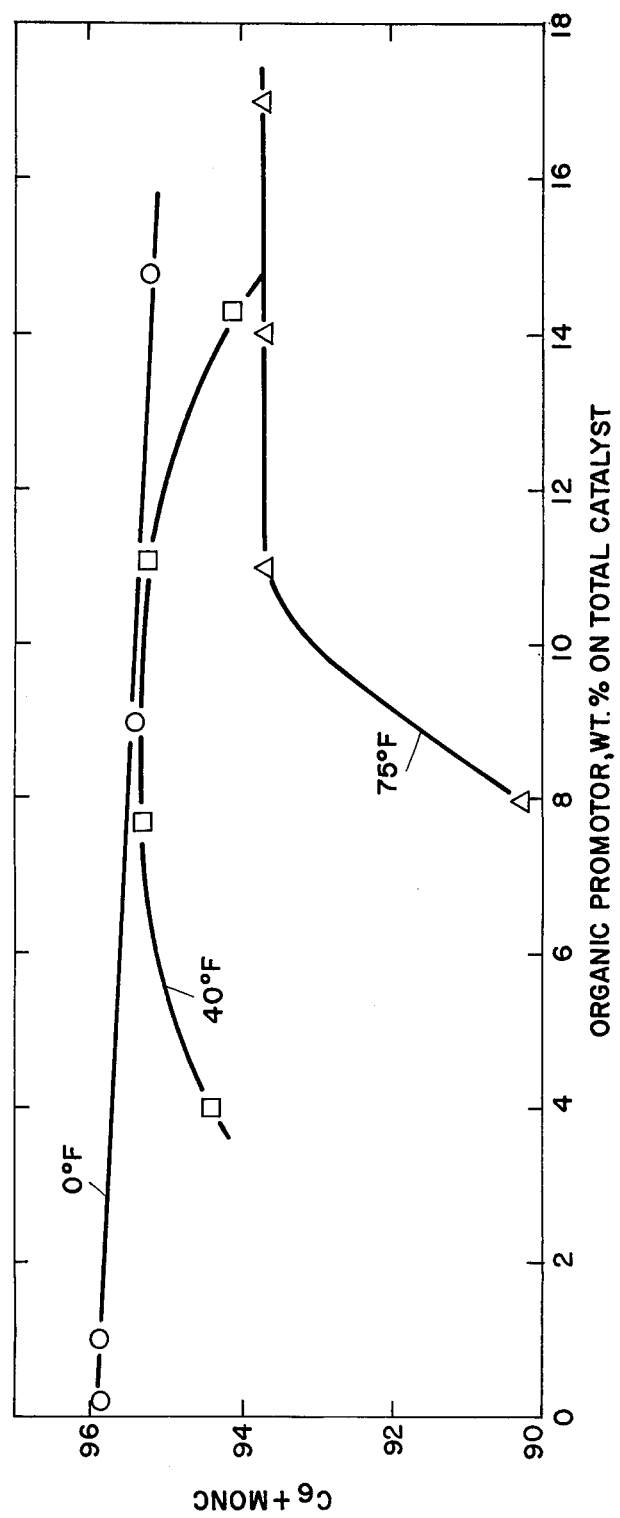

CATALYTIC ALKYLATION UTILIZING OLEFINIC, CONJUGATED CYCLIC HYDROCARBONS AS PROMOTER THEREIN

BACKGROUND OF THE INVENTION

1. Field of the Invention

The present invention relates to a hydrocarbon conversion process. More particularly, the invention relates to the alkylation of a paraffin with an olefin in the presence of an organic promoter that facilitates the formation of a high octane alkylate.

2. Description of the Prior Art

The use of catalytic alkylation processes to produce branched chain hydrocarbons having valuable antiknock properties that are suitable for use as gasoline blending components is well known in the petroleum refining art. Generally, the alkylation of saturated hydrocarbons, such as isoparaffins, with olefins is accomplished by contacting the reactants with an acid catalyst, such as sulfuric acid, fluorosulfuric acid or a halogen acid such as hydrofluoric acid to form a reaction mixture, settling said mixture to separate the catalyst from the hydrocarbons, and further separating the hydrocarbons, for example by fractionation, to recover the alkylation reaction product. The alkylation reaction product is normally a mixture of $C_5$-$C_{10}$ paraffins, often termed "alkylate", and typically contains a mixture of $C_8$-$C_9$ hydrocarbons, the composition depending upon the particular paraffin and olefin utilized. The formation of more highly branched hydrocarbons, e.g. trimethylpentanes, rather than less branched hydrocarbons, e.g. dimethylhexanes, is preferred because the former provide a higher quality gasoline blending stock.

It is well known in the art that as the alkylation reaction proceeds, there will form a material that is effective in promoting the alkylation reaction. This material has been given a variety of names, including red oil, sludge, organic sludge, acid oil and the like (see, for example, U.S. Pat. Nos. 2,245,038; 2,375,637; 2,396,853; 2,413,759; 2,415,717; 2,418,146; 3,780,130). It has also been suggested that the octane number of the alkylate from sulfuric acid alkylation is a function of the composition of the acid (see Albright, L.F. et al. "Alkylation of Isobutane With Butenes: Effect of Sulfuric Acid Compositions, " Ind. Eng. Chem. Process. Des. Develop., Vol. 11, No. 3, p. 446–450, 1972). However, none of the foregoing prior art teaches or suggests that the effectiveness of the organic promoter varies with temperature.

SUMMARY OF THE INVENTION

Now according to the present invention, it has been discovered that when a paraffin is alkylated with an olefin in a reaction zone in the presence of an organic promoter and an alkylation catalyst comprising (1) a halosulfuric acid of the formula $XSO_3H$, trihalomethanesulfonic acid of the formula $CX_3SO_3H$, X being a halogen, or mixture thereof, and (2) one or more moderators containing at least one oxygen atom per molecule, the effectiveness of said promoter in promoting the selectivity of high octane components in the alkylate varies with temperature. More particularly, it has been found that when the above alkylation catalyst is employed in the presence of an organic promoter at temperatures above about 0° F, the amount of organic promoter required to form high octane components increases with increasing temperature, assuming other variables, e.g., reactants and catalyst composition, remain substantially constant. At a temperature of 0° F, the promoter does not appear to affect alkylate quality. A preferred alkylation catalyst is fluorosulfuric acid and water.

BRIEF DESCRIPTION OF THE DRAWING

The single FIGURE is a graph showing the effect of the organic promoter content of the catalyst on alkylate octane number of the alkylate with temperature.

DETAILED DESCRIPTION OF THE INVENTION

The organic promoter referred to herein is a natural by-product of acid-catalyzed hydrocarbon reactions such as occur during alkylation and has been described in the literature as a conjunct polymer (see Miron, S. and Lee, R. J., "Molecular Structure of Conjugated Polymers", J. Chem, Eng. Data., Vol. 8, p. 150–160 (1963), the disclosures of which are incorporated herein by reference). These conjugate polymers are complex mixtures of olefinic, conjugated cyclic hydrocarbons that may be formed from any type of hydrocarbon except aromatics. More specifically, they are believed to be cyclic polyolefinic hydrocarbons with a high proportion of conjugated double bonds, no two of which are in the same ring. Five membered ring systems predominate, but larger, and possibly also smaller, rings are believed to be present.

As the alkylation reaction proceeds, organic promoter is formed and accumulates in the catalyst phase, causing an enhancement of alkylate product quality. The manner in which the promoter causes said enhancement is not known. However, after a period of time, a sufficient amount of the promoter is accumulated such that the strength of the alkylation catalyst is reduced, thereby causing a decrease in alkylate product quality. Accordingly, it has now been found that the use of at least 4 wt. % and preferably from 4 to about 20 wt. %, based on total catalyst, of the organic promoter with the alkylation catalyst described below facilitates the production of an alkylate of enchanced octane number at temperatures above 0° F, more preferably at temperatures of at least 30° F and in the range of from about 30° to about 85° F. More specifically, at a temperature ranging from about 30° to about 50° F, preferably about 35° to about 45° F, an alkylate of enchanced octane will be obtained when the concentration of organic promoter in the catalyst is maintained in the range of from about 4 to about 16 wt. %, preferably from about 4 to about 14 wt. %, more preferably from about 6 to about 12 wt. % and most preferably from about 8 to about 11 wt. % based on total catalyst. Similarly at a temperature ranging between about 65° and about 85° F, preferably between about 70° and about 80° F, the concentration of organic promoter in the catalyst should be at least 6 wt. % and in the range of from 6 to about 20 wt. %, preferably from about 6 to about 18 wt. %, more preferably from about 8 to about 16 wt. % and most preferably from about 9 to about 14 wt. % based on total catalyst. The term "total catalyst" refers to a catalyst containing organic promoter, strong acid and moderater.

Therefore, in one embodiment of the present invention, the organic promoter can be allowed to form naturally when fresh alkylation catalyst is contacted with hydrocarbons. However, the alkylate produced during such an initial period of operation will be of inferior quality relative to that obtained when at least 4 wt. % of the organic promoter is present. Therefore, rather than waiting for the promoter to accumulate as the alkylation reaction proceeds, it is desirable to add the promoter, preferably in the ranges mentioned above, during the induction period. Thus, the present invention can be used to provide a relatively uniform alkylate of enhanced product quality during initial as well as subsequent periods of operation.

The particular alkylation process employed in the present invention is that described in U.S. Pat. No. 3,887,635, the disclosures of which are incorporated herein by reference, which relates to the alkylation of a saturated hydrocarbon with an olefin in the presence of an alkylation catalyst mixture formed from a strong acid such as a halosulfuric acid of the formula $XSO_3H$, trihalomethanesulfonic acid of the formula $CX_3SO_3,H$, X being a halogen, or mixtures thereof and one or more moderators, generally containing at least one oxyen atom per molecule and including water, aliphatic and cycloaliphatic alcohols and ethers, aliphatic, cycloaliphatic and aromatic sulfonic and carboxylic acids and their derivatives and inorganic acids. The term "moderator" as used herein, is defined as a compound which, in combination with a strong acid, produces a catalyst system of increased selectivity, resulting in an alkylate of enchanced product quality. The addition of the moderator decreases the probability of undesirable and competitive side reactions.

Olefins that may be suitably employed in the present invention include $C_2$-$C_{12}$ terminal and internal monoolefins such as ethylene, propylene, butene-1, butene-2, isobutene, the isomeric pentenes and similar higher monoolefinic hydrocarbons of either a straight chain or a branched chain structure. Preferably, the $C_2$-$C_6$ monoolefins are used, although the highly-branched $C_7$-$C_{12}$ monoolefins may also be used. Cycloolefins may also be used. Although it is desirable from an economic standpoint to use the normally gaseous olefins as reactants, normally liquid olefins may be used. Thus, the alkylation process of the present invention contemplates the use of reactble polymers, copolymers, interpolymers, crosspolymers, and the like, of the above-mentioned olefins, such as, for example, the diisobutylene and triisobutylene polymers, the codimer of normal butylene and isobutylene, of butadiene and isobutylene, and the like. Mixtures of two or more of the olefins above described can be used as the process feedstock. Minor amounts of contaminants such as diolefins, acetylenes, mercaptans, aliphatic sulfur, water, caustic and the like may also be present. Such contaminants should be minimized, i.e. be less than 1 wt. % although larger amounts may be present, since each will cause increased acid consumption during subsequent alkylation.

Suitable paraffinic hydrocarbon feedstocks for use in the present invention comprise straight and/or branched chain $C_2$-$C_{10}$ paraffins such as hexane, butane and the like, and preferably, $C_4$-$C_6$ isoparaffins such as isobutane, isopentane, isohexane and the like. While open chain hydrocarbons are preferred, cycloparaffins such as cyclopropane may also be used. The use of various refinery cuts as feedstocks is also contemplated. Thus, $C_2$, $C_3$, $C_4$ and/or $C_5$ olefin cuts from thermal and/or catalytic cracking units; field butanes which have been subjected to prior isomerization and partial dehydrogenation treatment; refinery stabilizer bottoms; spent gases; normally liquid products from sulfuric acid or phosphoric acid catalyzed polymerization and copolymerization processes; and products, normally liquid in character, from thermal and/or catalytic cracking units, are all excellent feedstocks for the present alkylation process. Such feeds are preferably dried, i.e. about 5 to 15 wppm of water, before entering the reactor to control excess water buildup.

The alkylation catalyst moderators mentioned above may be used effectively with a wide variety of strong acids. Examples of strong acid components of the strong acid-moderator catalyst mixture include halosulfuric acid such as fluorosulfuric acid, chlorosulfuric acid and bromosulfuric acid; trihalomethanesulfonic acid such as trifluoromethanesulfonic acid, trichloromethanesulfonic acid and tribromomethanesulfonic acid; or mixtures thereof and the like. Preferred strong acids include fluorosulfuric acid, trifluoromethanesulfonic acid or mixtures thereof. In addition, the phosphorus analog of trihalomethanesulfonic acid, i.e. trihalomethanephosphonic acid, may be an effective strong acid.

The amounts of moderator used in forming the alkylation catalyst is an important variable in the production of high quality alkylate, the appropriate amount varying depending, in part, upon the alkylation temperature. Thus, for example, at temperatures between about 0° and 40° F, useful amounts of moderator can range between about 5 and 45 mole % based on acid (moles of moderator per 100 moles of acid), preferably between 10 and 30 mole % and still more preferably between 15 and 25 mole %, e.g. 20 mole %. In some instances, however, it may be desirable to use somewhat lower or higher amounts of moderator, e.g. 50 mole % based on acid, where, for example, increased catalyst selectivity is desired.

At higher alkylation temperatures, e.g. between about 40° and 100° F, increased amounts of moderator may be desirable due to the increased strong acid activity. Thus, an amount of moderator ranging between about 50 and 100 mol % based on acid at these higher temperatures may be employed. In fact, under appropriate conditions, these higher amounts of moderator may also be utilized at the lower temperatures disclosed hereinabove, if desired.

In the case of hydroxyl-containing moderators, (or moderators containing hydroxyl precursors, i.e. latent hydroxyl groups), amounts of moderator added to the strong acid may fall below the above-specified ranges. It appears that the efficiency of hydroxy compounds is directly related to the overall number of hydroxyl groups or latent hydroxyl groups present per molecule. Thus, ethanol with one hydroxyl group should have moderator activity similar to 0.5 mole of ethylene glycol with two hydroxyl groups. Hence, as the number of hydroxyl groups or latent hydroxyl groups per molecule of moderator increases, the required amount of moderator compound will decrease.

Although the broad concentration ranges are generally independent of the type of moderator used, the preferred or optimal range will vary depending on the structure of the moderator, the reaction temperature, the concentration and nature of the olefin in the feed and the olefin space velocity.

Typical operating conditions for the alkylation process described in U.S. Pat. No. 3,887,635 are summarized below:

|  | Suitable | Preferred |
|---|---|---|
| Total Pressure, atm. | 1 to 20 | 1 to 10 |

-continued

| | Suitable | Preferred |
|---|---|---|
| Olefin Space Velocity, V/Hr./V | 0.05 to 1000 | 0.05 to 1.0 |
| Contact Time, min | 0.002 to 60+ | 5 to 45 |
| Paraffin/Olefin Vol. Ratio in external feed | 2:1 to 200:1 | 5:1 to 20:1 |
| Paraffin/Olefin Vol. Ratio in Reaction Zone | 10:1 to 20000:1 | 20:1 to 2000:1 |

It is critical that the alkylation temperature be maintained above 0° F, preferably above 20° F and more preferably at least 30° F to obtain the benefits of the present invention. Preferably, the temperature will range from above about 0° to about 120° F or more, more preferably from about 20 to about 100° F and most preferably from about 30° to about 85° F.

In general, it is preferable to maintain the reactants substantially in the liquid phase although a vapor phase operation is also contemplated. Autorefrigerated reactors, indirectly refregerated reactors and the like may be employed to maintain liquid phase operation. Where the reaction is carried out at temperatures above about 10° F, it is necessary that the reaction be conducted under superatmospheric pressure, if both the reactants and catalyst are to be maintained substantially in the liquid state. The volume % of total catalyst in the reaction mixture or emulsion (when liquid phase operations are used) in the reactor can range from about 30 to 80 volume % based on total reaction mixture and preferably from about 50 to 70 volume %. The isoparaffin concentration, including alkylate, in the hydrocarbon phase (in a liquid phase process) can range from 40 to 100 volume % based on the total volume of the hydrocarbon phase and preferably from 50 to 90 volume %. Such isoparaffin concentrations can be maintained by recycling unreacted isoparaffin to the reactor.

The process may be carried out either as a batch or continuous type of operation, although it is preferred for economic reasons to carry out the process continuously. It has been generally established that in alkylation processes, the more intimate the contact between the feedstock and the catalyst the better the yield and quality of the saturated product obtained. With this in mind, the present process, when operated as a batch operation, is characterized by the use of vigorous mechanical stirring or shaking of the reactants and catalyst.

In continuous operations, in one embodiment, reactants may be maintained at sufficient pressures and temperatures to maintain them substantially in the liquid phase and then continuously forced through dispersion devices into the reaction zone. The dispersion devices may be jets, porous thimbles and the like. The reactants are subsequently mixed with the catalyst by conventional mixing means such as mechanical agitators and the like. After a sufficient time, the product can then be continuously separated from the catalyst and withdrawn from the reaction system while the partially spent catalyst is recycled to the reactor. If desired, a portion of the catalyst can be continuously regenerated or reactivated by any suitable treatment and returned to the alkylation reactor.

In another embodiment of the invention the catalyst may be incorporated with a suitable solid carrier or support. Any solid carrier may be used that is substantially inert to the catalyst under the reaction conditions. Active supports may be rendered inert by coating them with an inert material such as antimony trifluoride or aluminum trifluoride. Examples of such carriers include silica gel, anhydrous $AlF_3$, aluminum phosphate, carbon, coke, firebrick and the like. When supported catalysts are used, the reactants, in vapor and/or liquid form, are contacted with the catalyst particles at conversion conditions. The catalyst materials may be maintained in a fixed bed, moving bed or fluid bed reaction zone.

As in other processes, more accurate control of the quality of the final product may be obtained if the reaction system is provided with a recycling feature wherein the partially converted hydrocarbons are mixed with fresh feed and returned to the feed dispersion device in the reactor. However, due to the high conversion efficiency of the present catalyst system, it is preferred to effect alkylation in a once-through operation with short reaction times.

In general, reaction and/or recovery schemes and apparatus employed in conjunction with prior art liquid acid catalyst systems can be used with the catalyst systems of the present invention. Examples of potentially applicable process techniques and apparatus are described in U.S. Pat. Nos. 2,433,944; 2,479,366; 2,701,184; 2,717,913; 2,775,636; U.K. Pat. Nos.543,046; 577,869; 731,806; 738,348; 803,458; 804,966 and 881,892, the disclosures of which are incorporated herein by reference.

The present invention may be better understood by reference to the following examples which are presented for illustrative purposes only and are not intended to unduly restrict the limits of the claims appended hereto.

EXAMPLE 1

Effect of Organic Promoter at about 0° F.

An alkylation catalyst comprising fluorosulfuric acid and water was introduced into a continuous pilot plant sized reactor. The reactor contained baffles and was stirred with a flat blade turbine. Isobutane was charged to the reactor until the reactor was full of the hydrocarbon/catalyst mixture and the total pressure ranged between about 75 and 125 psig. The initial fill of isobutane served to minimize degradation reactions when the olefin was introduced. The alkylation catalyst represented about 60 volume % of the reactor charge. Stirring was initiated to emulsify the hydrocarbon/catalyst mixture and to allow same to equilibriate thermally. A small amount of organic promoter was formed when the isobutane was contacted with the catalyst. Hydrocarbon feedstock was then introduced into the mixture at which time additional organic promoter started to form and to accumulate in the catalyst phase. The hydrocarbon/catalyst emulsion was allowed to overflow into a settler wherein the hydrocarbon phase was separated from the catalyst phase. The settled catalyst phase was returned to the reactor while the hydrocarbon phase was withdrawn continuously and sampled periodically. The samples were analyzed by gas chromatography and the unleaded motor octane number (MONC) of the sample then calculated from the compositions obtained from the analyses. The results of these tests are shown in Table 1 below:

TABLE 1

| Run No. | 1 | 2 | 3 | 4 |
|---|---|---|---|---|
| Time of Sample, Hrs. since start-of-run | 14 | 36 | 281 | 393 |
| Catalyst | | | | |
| $H_2O$/acid, mole ratio | | | 0.3 | |
| Organic Promoter, wt.% | | | | |

TABLE 1-continued

| | | | | |
|---|---|---|---|---|
| on total catalyst | 0.2 | 1.0 | 9.0 | 14.8 |
| Feed Composition, Vol. % | | | | |
| Olefin (1) | 2.4 | 2.4 | 2.4 | 2.7 |
| Isobutane | 86.2 | 86.3 | 86.2 | 85.9 |
| n-paraffins | 11.4 | 11.3 | 11.4 | 11.4 |
| Operating Conditions | | | | |
| Temperature, °F. | −0.6 | −1.4 | −0.5 | 1.9 |
| Olefin Space Velocity, v/h/v (2) | 0.08 | 0.08 | 0.08 | 0.09 |
| $C_6$ + MONC | 95.9 | 95.9 | 95.4 | 95.2 |

(1) Olefin was butenes from a catalytic cracking unit.
(2) Volume of olefin per hour per volume of total catalyst in the reactor.

EXAMPLE 2

Effect of Organic Promoter at 40° F 189 cc of an organic promoter and a catalyst comprising fluorosulfuric acid and water was introduced by vacuum into a 315 cc stainless steel loop reactor immersed in a constant temperature bath. The organic promoter was obtained from spent alkylation catalyst and then added to the reactor to simulate an equilibrium catalyst mixture. As in Example 1, isobutane was then charged to the reactor until the reactor was full of hydrocarbon/catalyst mixture and the total pressure ranged between about 75-125 psig. The catalyst-isobutane mixture was then emulsified and circulated by a pump and allowed to equilibrate thermally. A hydrocarbon feedstock was introduced into the circulating emulsion and the hydrocarbon phase allowed to equilibrate. This required about two hours. The product was withdrawn from the reactor into a settler wherein the hydrocarbon phase was separated from the acid. The acid was returned to the reactor. A sample of the hydrocarbon phase was then analyzed by gas chromatography and the octane of said sample calculated from the compositions obtained therefrom. The reactor was then discharged and cleared. Additional runs using increased amounts of organic promoter were then made. The results from the experiment are shown in Table 2 below:

TABLE 2

| Run No. | 1 | 2 | 3 | 4 |
|---|---|---|---|---|
| Catalyst | | | | |
| $H_2O$/Acid, mole ratio | | 0.4 | | |
| Organic Promoter, wt. % on total catalyst | 4.0 | 7.7 | 11.1 | 14.3 |
| Feed Composition, vol.% | | | | |
| Olefin (1) | | 8.7 | | |
| Isobutane | | 80.7 | | |
| n-paraffins | | 10.6 | | |
| Operating Conditions | | | | |
| Temperature, °F | | 40 | | |
| Olefin Space Vel. v/h/v (2) | | 0.21 | | |
| $C_6$ + MONC | 94.4 | 95.3 | 95.2 | 94.1 |

(1) 25 Vol. % butene-1, 51 Vol. % butene-2, and 24 Vol. % isobutene.
(2) Same as in Example 1

EXAMPLE 3

Effect of Organic Promoter at 75°F.

The procedure of Example 2 was followed to obtain the results shown in Table 3.

TABLE 3

| Run No. | 1 | 2 | 3 | 4 |
|---|---|---|---|---|
| Catalyst | | | | |
| $H_2O$/acid, mole ratio | | 0.35 | | |
| Organic Promoter, wt.% on total catalyst | 8 | 11 | 14 | 17 |
| Feed Composition, vol. % | | | | |
| Olefin (1) | | 7.6 | | |
| Isobutane | | 82.6 | | |
| n-paraffins | | 9.8 | | |
| Operating Conditions | | | | |
| Temperature, °F | | 75 | | |
| Olefin Space Vel., v/h/v (2) | | 0.184 | | |
| $C_6$ + MONC | 90.3 | 93.7 | 93.7 | 93.7 |

(1) 20 Vol. % butene-1, 54 vol. % butene-2 and 26 Vol.% isobutene.
(2) Same as Example 1.

The results from Examples 1-3 are shown in the FIGURE as $C_6$+ MONC vs. wt. % organic promoter based on total catalyst. The FIGURE shows that at 0° F, the octane of the alkylate decreases monotonically in the presence of the organic promoter. However, at temperatures above about 0° F, alkylate octane number is enhanced in the presence of the organic promoter, the degree of enhancement varying with the amount of said promoter present as discussed above and as shown in the FIGURE. If desired, the variation of alkylation temperature with concentration of organic promoter in the total catalyst at maximum alkylate octane number may be obtained by cross-plotting the FIGURE.

What is claimed is:

1. In an alkylation process which comprises contacting a paraffin with an olefin at alkylation conditions and in the presence of an organic promoter comprising olefinic conjugated cyclic hydrocarbons and an alkylation catalyst comprising a strong acid catalyst selected from the group consisting of halosulfuric acid, trihalomethanesulfonic acid and mixtures thereof, the improvement which comprises the steps of:
   1. effecting substantially the entire alkylation at a temperature from above about 0° F to about 120° F by adding to the alkylation at least 4 to about 20 wt. %, based on total catalyst, of said organic promoter and
   2. recovering from step (1) an alkylate of enhanced product quality relative to that obtained when said alkylation is effected outside the conditons set forth in step (1).

2. The process of claim 1 wherein the temperature ranges from about 30° to about 50° F and the amount of organic promoter is maintained in the range of from 4 to about 16 wt. % based on total catalyst.

3. The process of claim 2 wherein the amount of organic promoter ranges from 4 to about 14 wt. % based on total catalyst.

4. The process of claim 1 wherein the temperature ranges from about 65° to about 85° F and the amount of organic promoter is maintained in the range of from 6 to about 20 wt. % based on total catalyst.

5. The process of claim 4 wherein the amount of organic promoter ranges from 6 to about 18 wt. % based on total catalyst.

6. The process of claim 1 wherein said alkylation catalyst is formed from said strong acid and the addition of about 5 to 100 mole %, based on acid, of (1) water, (2) a $C_1$–$C_7$ saturated aliphatic monohydroxy alcohol, or (3) a mixture of water and said alcohol.

7. The process of claim 1 wherein said alkylation catalyst is suppoted on a solid carrier.

8. The process of claim 6 wherein the alkylation catalyst comprises fluorosulfuric acid and about 5 to 100 mole % water, based on said acid.

9. In an alkylation process which comprises contacting a $C_2$–$C_{19}$ paraffin with an $C_2$–$C_{12}$ olefin in a reaction zone at alkylation conditions and in the presence of an organic promoter comprising olefinic conjugated cyclic hydrocarbons, and an alkylation catalyst comprising a strong acid catalyst selected from the group consisting of halosulfuric acid, trihalomethanesulfonic acid and mixtures thereof, the improvement which comprises the steps of:

1. effecting said alkylation at temperatures above about 0° F. to about 120° F with from 4 to about 20 wt. %, based on total catalyst, of said organic promoter initially added in said reaction zone and
2. receovering from step (1) an alkylate of enhanced product quality relative to that obtained when said alkylation is effected outside the conditon set forth in step (1).

10. The process of claim 9 wherein said temperatures range from about 30° to about 85° F.

11. The process of claim 9 wherein said temperatures range from about 30° to about 50° F and the amount of organic promoter is maintained in the range of from 6 to about 14 wt. % based on total catalyst.

12. The process of claim 11 wherein the amount of organic promoter ranges frm about 8 to about 11 wt. % based on total catalyst.

13. The process of claim 9 wherein the temperature ranges from about 65° to about 85° F and the amount of organic promoter is maintained in the range of from about 8 to about 16 wt. % based on total catalyst.

14. The process of claim 13 wherein the amount of organic promotor ranges from about 9 to about 14 wt. % based on total catalyst.

15. The process of claim 9 wherein said alkylation catalyst is formed from said fluorosulfuric acid and the addition of about 5 to 100 mole % water, based on said acid.

16. The process of claim 9 wherein the $C_2$–$C_{10}$ paraffin is a $C_2$–$C_4$ isoparaffin.

* * * * *